US00PP28022P3

(12) United States Plant Patent
Castellarin et al.

(10) Patent No.: US PP28,022 P3
(45) Date of Patent: May 16, 2017

(54) GRAPEVINE NAMED 'SAUVIGNON RYTOS'

(50) Latin Name: ***Vitis×vinifera* (hybrid)**
Varietal Denomination: SAUVIGNON RYTOS

(71) Applicants: Università degli Studi di Udine, Udine UD (IT); Istituto di Genomica Applicata, Udine UD (IT)

(72) Inventors: Simone Diego Castellarin, Vancouver (CA); Guido Cipriani, Faedis (IT); Gabriele Di Gaspero, Cividale del Friuli UD (IT); Michele Morgante, Tricesimo UD (IT); Enrico Peterlunger, Codroipo UD (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 14/545,100

(22) Filed: Mar. 26, 2015

(65) Prior Publication Data

US 2016/0242339 P1 Aug. 18, 2016

(30) Foreign Application Priority Data

Feb. 13, 2015 (QZ) ..... PBR 2015/0359

(51) Int. Cl.
*A01H 5/08* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Foley & Lardner LLP

(57) ABSTRACT

A new and distinct variety of grapevine named 'SAUVIGNON RYTOS', primarily adapted to the growing conditions of the temperate regions, and characterized by its medium vigor; semi-erect growth habit; wedge-shaped leaves with medium texture; small cylindrical shaped green-yellow berry clusters with a golden nuance on the sunny side of the berries; early maturing, soft berry flesh with no coloration and neutral taste primarily for winemaking; and resistance to winter temperatures (to −23° C.), resistance to downy mildew and tolerance to powdery mildew.

4 Drawing Sheets

Latin name of the genus and species of the plant claimed: *Vitis×vinifera* (hybrid).

Variety name: 'SAUVIGNON RYTOS'.

BACKGROUND OF THE INVENTION

The present invention relates to a new and distinct summer/fall bearing grapevine variety, botanically known as *Vitis vinifera*, and hereinafter referred to by the name 'SAUVIGNON RYTOS'.

The new grapevine 'SAUVIGNON RYTOS' is a product of a controlled breeding program conducted by the inventors in Udine, Italy. The objective of the breeding program was to develop a new grapevine variety particularly characterized by resistance to cold (<−20° C.), resistance to downy mildew (*Plasmopara viticola*), and tolerance to powdery mildew (*Uncinula necator*).

The new grapevine 'SAUVIGNON RYTOS' originated from a cross made by the inventors in 2002 in Udine, Italy. The female or seed parent is the grapevine variety *Vitis vinifera* cv. 'Sauvignon' (unpatented), and the male or pollen parent is the grapevine variety *Vitis* cv. 'Bianca' (Eger 2×Bouvier) (unpatented).

The new grapevine 'SAUVIGNON RYTOS' was discovered and selected by the inventors as a single flowering plant within the progeny of the stated cross in a controlled environment in 2002 in Udine, Italy. Asexual reproduction of the new grapevine variety by grafting was first performed in February 2004 in Rauscedo, Friuli Venezia Giulia region, Italy, and has demonstrated that the combination of characteristics as herein disclosed for the new cultivar are firmly fixed and retained through successive generations of asexual reproduction. The new cultivar reproduces true to type.

SUMMARY OF THE INVENTION

'SAUVIGNON RYTOS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required to produce and maintain a strong vigorous plant with consistent fruit production from April through November on primocanes and in the ensuing year from April through November on the floricanes.

The following traits have been repeatedly observed and are determined to be unique characteristics of 'SAUVIGNON RYTOS', which in combination distinguish this grapevine plant as a new and distinct variety.

1. Medium vigor;
2. Semi-erect growth habit;
3. Medium size wedge-shaped leaves, with a pale green upper and lower surface and medium texture;
4. Small, dense cylindrical clusters with 1 small size wing; early maturing, green-yellow berries with golden nuances on the sunny side of the berries, soft flesh, neutral taste, and no flesh coloration, primarily used for winemaking.

5. Elliptic cross section, brownish color primocanes and floricanes with no lenticels and short-medium internodes (10-11 cm) of 10 mm diameter.
6. Harvesting time in early September (Middle Friuli, North-Eastern Italy); and
7. Resistance to winter temperature (−23° C.), resistance to downy mildew, and tolerance to powdery mildew.

Plants of the new grapevine 'SAUVIGNON RYTOS' differ from plants of the parents, *Vitis vinifera* 'Sauvignon' (unpatented) and 'Bianca' (unpatented), in the following characteristics described in Table 1.

TABLE 1

Comparison with Parent Varieties

| Characteristic | New Cultivar 'SAUVIGNON RYTOS' | Female Parent 'Sauvignon' (unpatented) | Male Parent 'Bianca' (unpatented) |
|---|---|---|---|
| vigor | medium | medium | strong |
| growth habit | Semi-erect | Semi-erect | semi-erect |
| leaf | medium size, pale green color (upper surface), pale green color (lower surface), wedge-shaped, medium texture, no hairs in both surfaces | Medium size, green color (upper surface), pale green color (lower surface), circular shape, medium texture, prostrate hairs present in upper surface and in lower surface | medium size, pale green color (upper surface), green color (lower surface), no hairs in both surfaces, wedge-to-kidney-shaped, medium texture |
| cluster | Low size, cylindrical with 1-2 middle size wings, very dense, berry skin with green-yellow color, soft flesh, neutral taste, no flesh coloration | Low size, cylindrical-conical with 1-2 wings, dense, berry skin with green-yellow color, slightly firm flesh, herbaceous taste, no flesh coloration | Low size, conical, with 1-2 wings, medium bunch density, berry skin with green-yellow color, slightly firm flesh, neutral taste, no flesh coloration |
| primocane and floricane | elliptic cross section, brownish color, lenticels: absent, short-middle internodes (10-11 cm), diameter: 10 mm | Circular section, brownish color, lenticels: absent, short-middle internodes (10-11 cm), diameter 10 mm | oblate cross section, brownish color, lenticels: absent, medium internodes, diameter small (about 8 mm) |
| harvesting time | Medium (early September in Middle Friuli, North-Eastern Italy) | Medium (Early September in Middle Friuli, North-Eastern Italy) | early (end of August to mid-September in Middle Friuli, North-Eastern Italy) |
| resistances | resistant to winter temperature (−23° C.), resistant to downy mildew, tolerant to powdery mildew, | Average resistance to winter temperature (−15° C.), susceptible to downy mildew, susceptible to powdery mildew | resistant to cold not known; resistant to downy mildew, resistant to powdery mildew |

Of the many commercial cultivars known to the present inventor, the most similar to the new grapevine 'SAUVIGNON RYTOS' is the female parent 'Sauvignon', to which a comparison has been provided above.

BRIEF DESCRIPTION OF THE PHOTOGRAPHS

The accompanying photographs illustrate the overall appearance of the new grapevine 'SAUVIGNON RYTOS' showing the colors as true as is reasonably possible with colored reproductions of this type. Colors in the photographs may differ slightly from the color values cited in the detailed botanical description, which accurately describe the color of 'SAUVIGNON RYTOS'.

DETAILED BOTANICAL DESCRIPTION

Figure 1A:
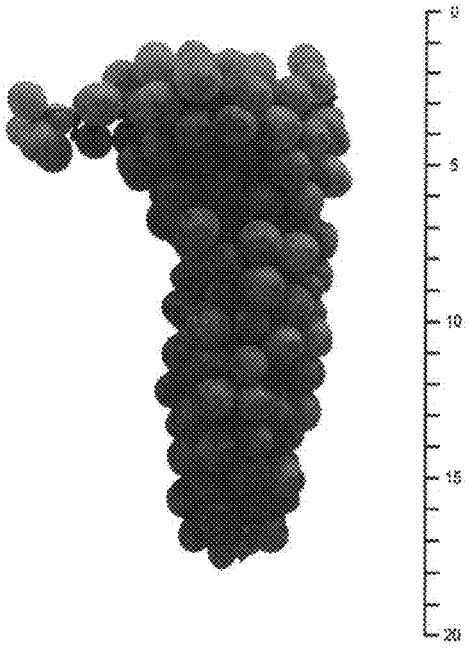
FIG. 1A and FIG. 1B show a typical fruit cluster of 'SAUVIGNON RYTOS', taken on Sep. 7, 2012 in Udine, Italy.
Figure 1B:
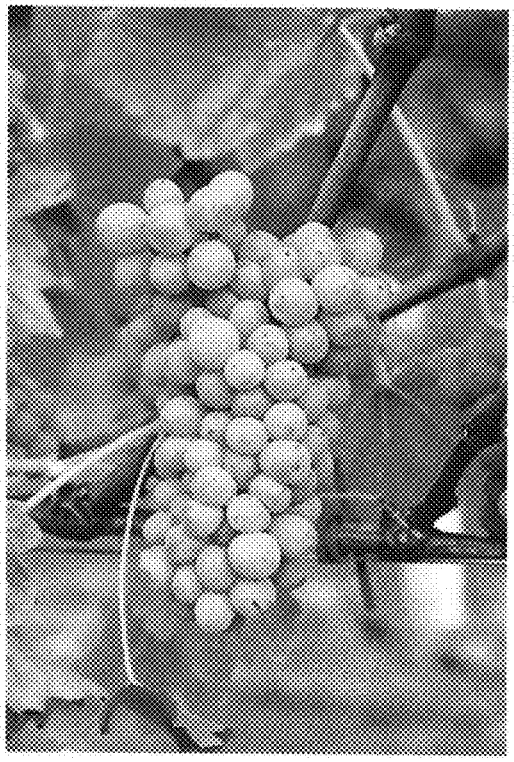
Figure 2:
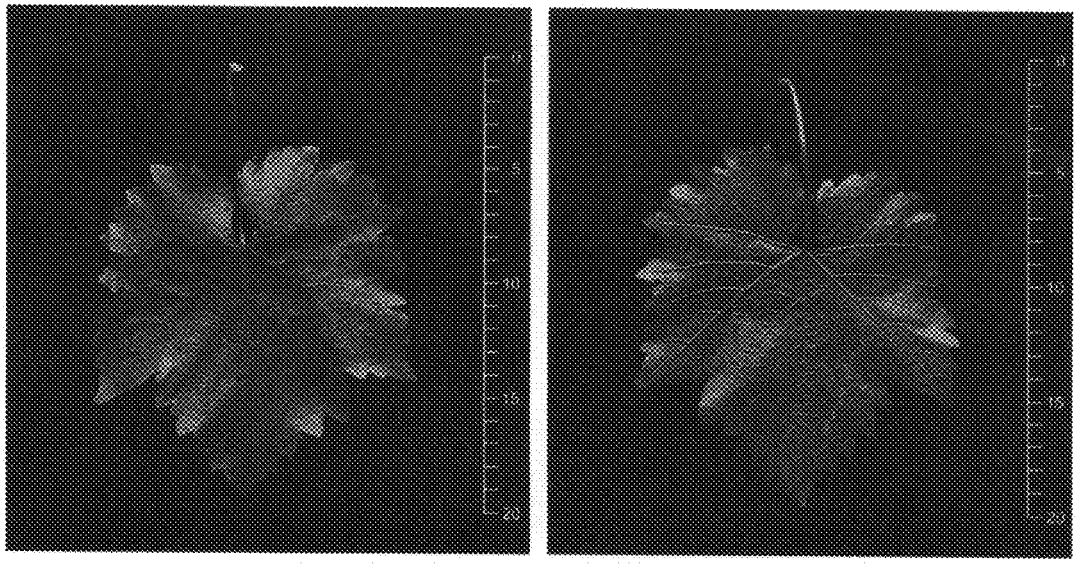
FIG. 2 shows a typical mature leaf (upper surface, left and lower surface, right) of 'SAUVIGNON RYTOS', taken on Jun. 15, 2012 in Udine, Italy.
Figure 3:
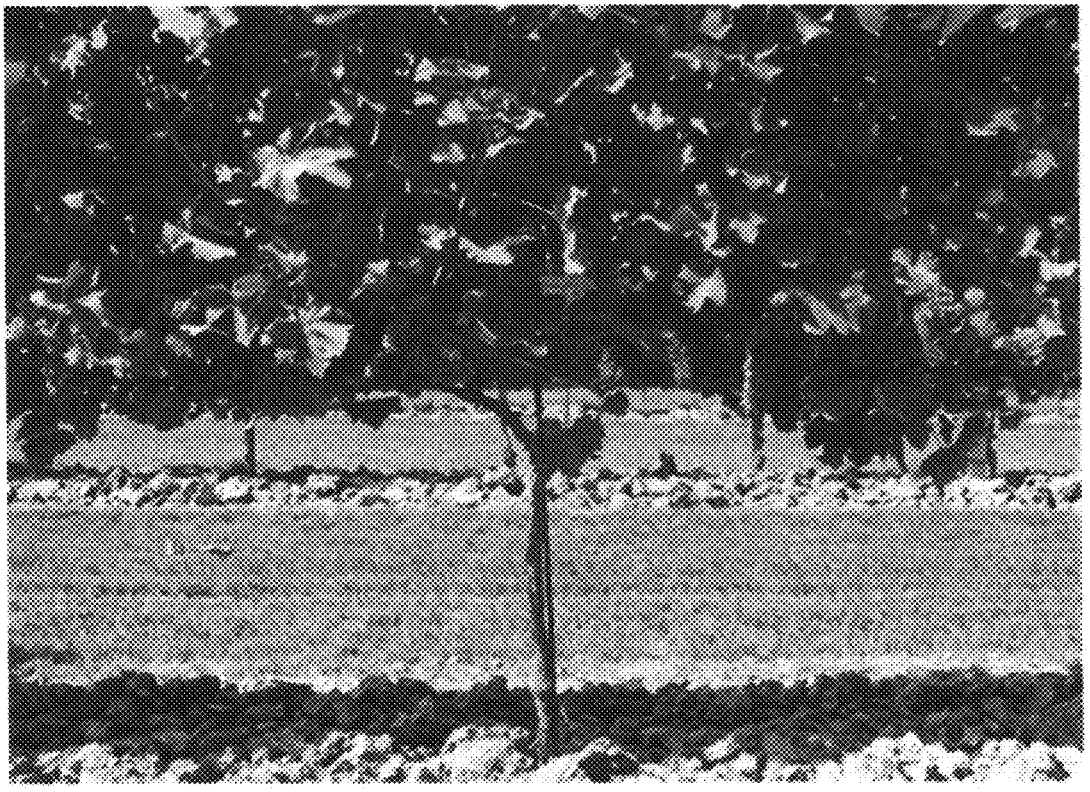
FIG. 3 shows a typical mature vine of 'SAUVIGNON RYTOS', taken on Aug. 3, 2012.
Figure 4:
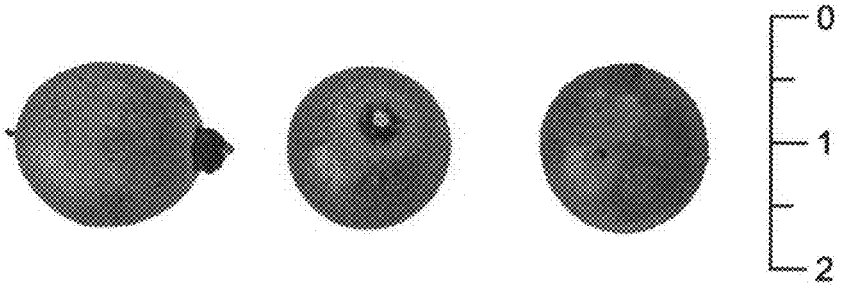
FIG. 4 shows a close-up view of typical mature fruit of 'SAUVIGNON RYTOS', taken on Aug. 25, 2012 in Udine, Italy

The following description of 'SAUVIGNON RYTOS' unless otherwise noted, is based on observations taken during the 2011, 2012, and 2013 growing seasons(s) in Udine (UD), Italy and Fossalon di Grado (GO), Italy, from plants dug from a nursery located in Rauscedo (PN), Italy during the beginning of December 2007 and planted approximately 16 to 20 weeks later in Udine (UD), Italy and Fossalon di Grado (GO), Italy. The phenotypical descriptions and color designations stated for the new variety may vary, depending upon variations in environmental factors, including weather (temperature, humidity and light intensity), day length, soil type, location and cultural conditions. 'SAUVIGNON RYTOS' has not been observed under all possible environmental conditions.

Color references are made to The Royal Horticultural Society Colour Chart (R.H.S.), (Edition V, 2007), except where general colors of ordinary significance are used.

| Characteristic | 'SAUVIGNON RYTOS' | 'SAUVIGNON' (unpatented) |
|---|---|---|
| GENERAL | | |
| Resistance to pest/disease | Resistant to downy mildew, tolerant to powdery mildew | Susceptible to downy mildew and to powdery mildew |
| Resistance to natural elements | Resistant to winter cold down to −23° C. | Resistant to winter cold down to −15° C. |
| VINE | | |
| Vigor | Medium | medium |
| Trunk diameter | 6 cm | 6.5 cm |
| Bark | | |
| color | RHS 177B | Dark brown |
| underbark color | RHS 179B | Light brown |
| texture | n.a. | n.a. |
| Canes | | |
| length | Internode length cm 10.5 | Internode length about cm 11 |
| width | 10 mm | 8 mm |
| Shoots | | |
| shape | Semi-erect, elliptic cross section, surface with stripes, nodes and internodes without hairs | Semi-erected, cross section: circular, surface: smooth, nodes and internodes without hairs |
| color | Internodes with red (RHS 185B) and green (RHS 144B) pigmentation on the dorsal side and green on the ventral (RHS 144B) side | Internodes with green color on ventral and dorsal side, nodes with green ventral and dorsal side |

-continued

| Characteristic | 'SAUVIGNON RYTOS' | 'SAUVIGNON' (unpatented) |
|---|---|---|
| Tendrils | | |
| form | Bifid | bifid |
| color | RHS145C and RHS184D | Green |
| texture | normal | normal |
| number | 2 or <2 consecutive | 2 or <2 consecutive |
| Buds | | |
| size | average | average |
| shape | round | round |
| color | RHS139C and RHS181A | Light brown |
| number | 2/node | 2/node |
| time of budbreak | medium | early-medium |
| LEAVES | | |
| Size | medium | medium |
| Number of leaflets | 3-5 | 5 |
| Glossiness | Medium-high | medium |
| Cross section shape | V-shaped | V-shaped |
| Color (immature) | | |
| Upper surface | RHS 143B and RH5185B | Pale green |
| Under surface | RHS 143B and RH5185B | Pale green |
| Color (mature) | | |
| Upper surface | RHS 143B | Medium green |
| Under surface | RHS 143C | Darker green |
| Petiole | | |
| Length (cm) | 6.2 | 6.0 |
| Color (upper surface) | RHS 145B and RHS185B | green |
| Color (under surface) | RHS 145B and RHS185B | green |
| Stipule orientation | n.a. | n.a. |
| FLOWERS | | |
| Flowering period (time of beginning of flowering) | End of May | End of May |
| Sex | hermaphrodite | hermaphrodite |
| Size | Average | average |
| Diameter (cm) | 0.3 (stamens) | 0.3 (stamens) |
| Stamen color | RHS4 4D | |
| Pistil color | RHS 149A | |
| Fragrance | average | average |
| Flower number (at 3rd node from tip of lateral mean and range) | n.a. | n.a. |
| Petals | | |
| Length (cm) | n.a. | n.a. |
| Width (cm) | n.a. | n.a. |
| Overall shape | calyptra | calyptra |
| Calyptra Color | RHS 134A | green |
| Sepals | | |
| Length (cm) | n.a. | n.a. |
| Width (cm) | n.a. | n.a. |

-continued

| Characteristic | 'SAUVIGNON RYTOS' | 'SAUVIGNON' (unpatented) |
|---|---|---|
| Overall shape | n.a. | n.a. |
| Color (immature) | n.a. | n.a. |
| Upper surface | | |
| Under surface | | |
| Color (mature) | n.a. | n.a. |
| Upper surface | | |
| Under surface | | |
| Pedicel | | |
| Length (mm) | 7 | 7 |
| Color | RHS 145C | green |
| FRUIT | | |
| Primocane time of fruiting (1st pick) | September 17th | September 7th |
| Clusters | | |
| cluster weight | Low (g 192) | Low (g 230) |
| cluster shape | cylindrical | conical |
| cluster length | mm 180 | medium |
| avg. berries per cluster | 150 | 220 |
| avg. clusters per shoot | 2 | 2 |
| Berries | | |
| Berry size | g 1.3 | g 1.0 |
| Berry length (cm) | 1.68 | 1.50 |
| Berry width (cm) | 1.40 | 1.50 |
| Overall shape of berry | ellipsoid | globose |
| Berry Texture | soft | soft |
| Berry Skin Color (immature) | RHS 137C | green |
| Berry Skin Color (mature, at 19° Bx) | RHS 2C and RHS 154C | green |
| Berry Flesh Color | RHS 148B | |
| Soluble solids (%) | 22.6 | 21.1 |
| Titratable acidity (as g/L tartaric acid) | 4.8 | 5.7 |
| Sugar/acid ratio | 4.7 | 3.7 |
| Firmness | soft | soft |
| Seeds | 2-3 | 2-3 |
| Seed Color | RHS 163B and RHS165A | |
| Skin cracking? | no | rarely |
| Juice color | transparent | transparent |
| Berry taste | Neutral | neutral |
| Eating quality | n.a. | n.a. |
| Berry uses | wine | wine |
| Shipping quality | n.a. | n.a. |

What is claimed is:

1. A new and distinct grapevine, referred to as 'SAUVIGNON RYTOS', as herein described and illustrated by the characteristics set forth above.

* * * * *